(12) United States Patent
Ellerbee (10) Patent No.: US 8,446,593 B1
(45) Date of Patent: May 21, 2013

(54) OPTICAL COHERENCE TOMOGRAPHY SYSTEM AND METHOD THEREFOR

(75) Inventor: Audrey Ellerbee, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 66 days.

(21) Appl. No.: 13/160,879

(22) Filed: Jun. 15, 2011

Related U.S. Application Data

(60) Provisional application No. 61/355,248, filed on Jun. 16, 2010.

(51) Int. Cl.
*G01B 11/02* (2006.01)
(52) U.S. Cl.
USPC .......................................... 356/497; 356/479
(58) Field of Classification Search
USPC ............................ 356/497, 479, 504, 505, 511
See application file for complete search history.

(56) References Cited

U.S. PATENT DOCUMENTS

| | | | | |
|---|---|---|---|---|
| 7,355,716 | B2 * | 4/2008 | de Boer et al. | 356/479 |
| 7,602,500 | B2 * | 10/2009 | Izatt et al. | 356/497 |
| 2011/0080591 | A1 * | 4/2011 | Johnson et al. | 356/479 |

OTHER PUBLICATIONS

Yelin et al., "Three-dimensional spectrally encoded imaging", "Optics Letters", Dec. 1, 2003, vol. 28, No. 23, Publisher: Optical Society of America, Published in: US.
Tsia et al., "Performance of serial time-encoded amplified microscope", "Optics Express", May 10, 2010, vol. 18, No. 10, Publisher: Optical Society of America, Published in: US.
Goda et al., "Serial time-encoded amplified imaging for real-time observation of fast dynamic phenomena", "Nature—Letters", Apr. 30, 2009, pp. 1145-1150, vol. 458, Publisher: Macmillan Publishers Limited.
Yelin et al., "Volumetric sub-surface imaging using spectrally encoded endoscopy", "Optics Express", Feb. 4, 2008, vol. 16, No. 3, Publisher: Optical Society of America, Published in: US.

* cited by examiner

*Primary Examiner* — Gregory J Toatley
*Assistant Examiner* — Rufus Phillips
(74) *Attorney, Agent, or Firm* — Kaplan Breyer Schwarz & Ottesen, LLP (57) ABSTRACT

A method for increasing the imaging rate for an optical coherence tomography system is disclosed. The method comprises generating an interferometric signal by interrogating each of M image points on a sample with a plurality of wavelength bands that are collectively spectrally interleaved, time encoding the interferometric signal, and sampling the time-encoded interferometric signal at a single detector.

20 Claims, 6 Drawing Sheets

OPTICAL COHERENCE TOMOGRAPHY SYSTEM AND METHOD THEREFOR

CROSS REFERENCE TO RELATED APPLICATIONS

This application claims the benefit of U.S. Provisional Patent Application Ser. No. 61/355,248, filed Jun. 16, 2010, entitled "A Spectral Encoding-based Approach to Real-time Volumetric Imaging with Optical Coherence Tomography," which is incorporated herein by reference.

If there are any contradictions or inconsistencies in language between this application and one or more of the cases that have been incorporated by reference that might affect the interpretation of the claims in this case, the claims in this case should be interpreted to be consistent with the language in this case.

FIELD OF THE INVENTION

The present invention relates to optical coherence tomography in general, and, more particularly, to Fourier-domain optical coherence tomography.

BACKGROUND OF THE INVENTION

Optical coherence tomography (OCT) is an optical imaging method that has become an increasingly popular diagnostic tool in areas such as the biological, biomedical, medical screening, and vision-care. It utilizes low-coherence optical interferometry to enable non-invasive imaging of micron-scale microstructure inside biological tissue. In recent years, OCT has rapidly become competitive with radiography, ultrasound and magnetic resonance imaging in the biological and biomedical imaging communities due, in part, to its relatively low cost and high-resolution, in-vivo capabilities, as well as its lack of ionizing radiation. In the vision-care arena, for example, OCT is used to non-invasively image the human eye fundus, thereby facilitating diagnosis of retinal pathologies, such as macular degeneration, glaucoma, retinitous pigmentosa, and the like.

Early OCT systems were typically time-domain systems based on a relatively simple implementation of the classic Michelson interferometer. In such an interferometer, an input light signal is split into a reference arm and a sample arm, each of which reflects light back to a beam combiner that combines the two reflected light signals to generate an interference pattern that is then sampled by a detector. Only light that travels the same length in each of the reference arm and sample arm combine such that it results in a strong signal at the detector. In the reference arm, light is directed toward a movable reference mirror, which continuously reflects light back toward the detector. The length of the reference arm depends on the position of this mirror. In the sample arm, only light reflected by sub-surface features in the sample is returned toward the detector. The length of the sample arm, therefore, is based on the positions of features within the sample tissue. As a result, by scanning the reference mirror at a constant speed to change the length of the reference arm, the depth of each feature in the sample tissue is encoded in time by the position of the reference mirror, as represented in the interference pattern that is subsequently sampled by the detector.

Unfortunately, while early time-domain OCT techniques were promising, their complexity and time-intensive nature represented a significant limitation to their widespread adoption. Recent advances in OCT, however, have reduced the time necessary for a scan enabling the generation of high-resolution, cross-sectional (i.e., two-dimensional) images of sub-surface tissue microstructure.

Fourier-domain OCT (FD-OCT) introduced a scheme wherein a detector samples a resultant interferometric signal as a function of wavelength rather than position (i.e., time). This improved sampling scheme enables faster imaging with higher sensitivity. Typically, the broadband light is provided by either a broadband light source or a light source that sweeps through a range of optical frequencies (i.e., a swept source). In a swept-source system, each point of a two-dimensional area of a sample is sequentially illuminated with a monochromatic beam whose optical frequency is a function of time to generate an interferometric signal of intensity versus wavenumber, k (k is proportional to the inverse of wavelength). A mathematical algorithm, referred to as a Fourier transform, is then used to convert the interferometric signal to a plot of intensity versus depth in the tissue at the measured point. By virtue of its parallel nature, an FD-OCT system can generate a cross-sectional image of tissue features faster than early time-domain OCT systems.

The advantages of swept-source implementations over time-domain OCT include improved signal-to-noise ratio and faster scan rates. The wavelength-scanning speed of a swept-source FD-OCT system can exceed a wavelength sweep rate of 300 kHz using a research-grade Fourier-domain Mode-locking (FDML) laser. As a result, an FDML-based swept-source system is capable of generating a 100×100×512 pixel-volume dataset at 30 Hz (i.e., in real time). Unfortunately, this cross-sectional area is too small to have significant utility in many applications. Using a commercially available swept source, which has a typical sweep rate of approximately 50 kHz, an FD-OCT system could develop a 100×100×512 pixel-volume dataset at only 5 Hz, which is much slower than necessary for real-time imaging.

Spectral-domain OCT represents another approach for improving imaging speed. In a spectral-domain OCT system, light collected from all depths at each point of a two-dimensional area of a sample is dispersed across a linear array of detectors such that the information is sampled as a function of wavelength. Unfortunately, each point to be imaged must be integrated fully on the detector before another point can be imaged. As a result, the time required for detector integration and readout represents a significant bottleneck. Further, although no wavelength scanning is needed (in contrast to a swept-source system), the speed of the detectors used in spectral domain OCT systems are typically slower than the scan rate of the sources in swept-source systems. For example, typical commercial systems have equivalent line rates of 29 kHz, which corresponds to a maximum image rate of 2.9 Hz for a 100×100×512 volume dataset. Recent improvements in commercially available linear detectors have improved the potential line rate to 92 kHz; however, this corresponds to a maximum image rate of only approximately 9.2 Hz, still woefully inadequate for real-time imaging applications.

Spectral encoded endoscopy (SEE) is a particular implementation of spectral-domain OCT that uses a single optical fiber and miniature diffractive optics to obtain endoscopic images through small diameter probes. Using spectral-domain interferometry, SEE is furthermore capable of three-dimensional volume imaging at video rates. In a SEE system, light from a swept source or broadband source is dispersed linearly along N image points of a two-dimensional area of a sample. As a result, each of the image points is illuminated by 1/N of the wavelength range of the source light. Although SEE enables high-speed volumetric imaging, the resolution of the image suffers since depth resolution depends on the total wavelength range used to interrogate an image point.

Even with the advances in OCT modalities, real-time imaging of three-dimensional volumes of reasonable size and resolution still eludes the OCT community.

SUMMARY OF THE INVENTION

The present invention enables high-speed OCT image formation while maintaining good depth resolution. Embodiments of the present invention are well suited for developing three-dimensional images, in real time, in application areas such as ophthalmology, developmental biology, cancer screening, endoscopy, cardiology, cellular dynamics, and the like.

The present invention enables interrogation of a row of M image points on a sample via the sample arm of an interferometer, wherein each image point is interrogated with a plurality of wavelength bands, and wherein the wavelength bands are collectively spectrally interleaved. Light signals reflected from each image point are based on surface and sub-surface features at that image point. Each of the reflected light signals is combined with a corresponding reference signal in the reference arm of the interferometer such that the M reflected signals collectively define an interferometric signal. The interferometric signal is time encoded and sampled at a single detector to generate M output signals that are uniquely based on the M image points. The single detector is characterized by a sampling bandwidth sufficient to satisfy the Nyquist sampling criterion for the interferometric signal.

In some embodiments, the spectral information from the M image points is time encoded by scanning a swept-source input optical signal repeatedly over the image points during a single sweep period of the swept-source input optical signal. In some embodiments, the spectral information from the M image points is time encoded by passing an interferometric signal comprising light reflected from all of the image points through a chromatic dispersive element.

In some embodiments, N rows of M image points are raster scanned and sampled with the single detector and a processor processes the output of the detector to form a three-dimensional image of the sample. By virtue of the parallel interrogation of the M image points, embodiments of the present invention derive an M-fold increase in imaging speed over traditional spectral domain and swept-source OCT systems.

An embodiment of the present invention comprises a method wherein a swept-source signal is scanned along a row comprising a plurality of image points on a sample. The swept-source signal is a periodic signal of sweep periods, wherein the wavelength of the signal is steadily swept through a wavelength range during each sweep period. The swept-source signal is scanned along the row many times during a single sweep time of the swept source. As a result, each image point in the row is illuminated by wavelengths that substantially span the entire wavelength range of the swept-source signal; however, each image point is illuminated by a different set of wavelength bands, wherein the elements of these different sets of wavelength bands are spectrally interleaved.

A single high-speed detector receives light reflected from each image point. For each image point, the detector converts the reflected light into an electrical output signal. A processor processes this plurality of electrical output signals to form a cross-sectional image of the sample along the row. By interrogating multiple rows (e.g., by raster scanning the swept-source signal across the rows) a three-dimensional image of the sample is produced. A detector is selected that has a bandwidth sufficient to sample the light reflected from all of the interrogated image points. In some embodiments, a single detector samples all interrogated image points at a rate suitable to satisfy the Nyquist criterion and at a rate sufficient to produce an image of the sample at a rate of at least 30 Hz.

Since depth resolution is based on the spectral bandwidth of the light used to interrogate an image point, the present invention enables an M-fold increase in image acquisition rate (where M is the number of image points in a row) without suffering a significant loss of depth resolution.

In some embodiments, the swept-source signal is scanned along the image points by a scanning mirror. In some embodiments, the swept-source signal is scanned along the image points by a diffractive element, such as a diffraction grating, prism, and the like.

An embodiment of the present invention comprises a method of forming an image of a sample via optical coherence tomography, the method comprising. interrogating a first image point of M image points on the sample with a first plurality of wavelength bands that substantially collectively span a first wavelength range, wherein the first image point reflects a first reflected signal that is based on the surface and sub-surface structure at the first image point; interrogating a second image point of the M image points on the sample with a second plurality of wavelength bands that substantially collectively span the first wavelength range, wherein the second image point reflects a second reflected signal comprising a second plurality of spectral components that are based on the surface and sub-surface structure at the second image point, and wherein the second plurality of wavelength bands and the first plurality of wavelength bands are spectrally interleaved; forming an interferometric signal based on M reflected signals, wherein the M reflected signals include the first reflected signal and the second reflected signal; time encoding the interferometric signal; and providing M output signals, wherein each of the M output signals is based on a different one of the M image points, and wherein each of the M output signals is provided by sampling the interferometric signal at a first detector.

DETAILED DESCRIPTION

Figure 1A:
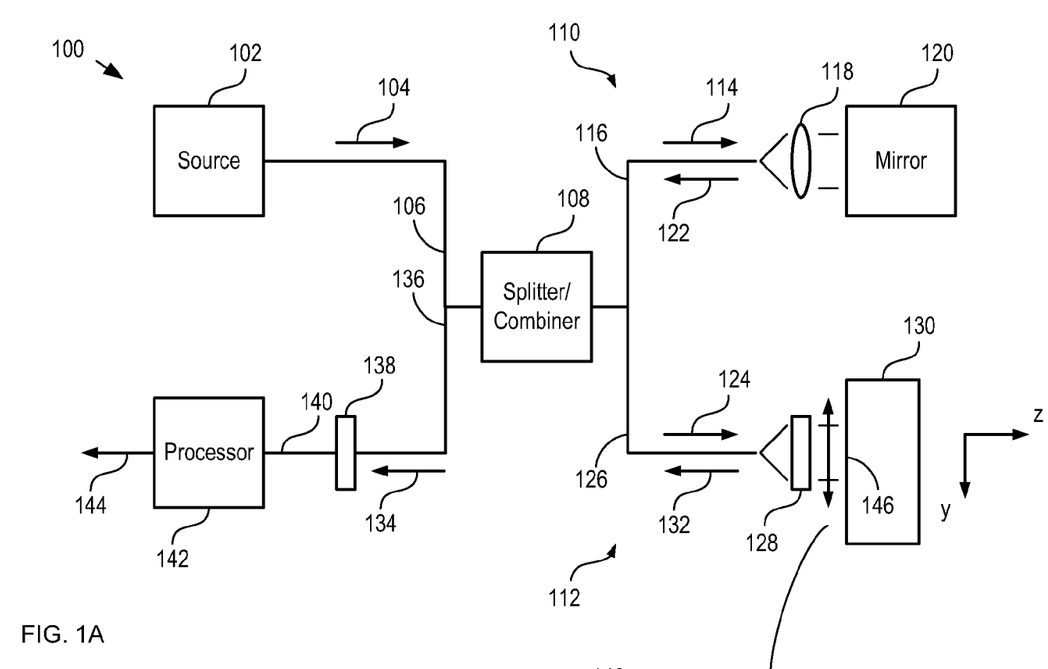
FIG. 1A depicts a schematic diagram of a portion of an OCT system in accordance with an illustrative embodiment of the present invention.

FIG. 1A depicts a schematic diagram of a portion of an OCT system in accordance with an illustrative embodiment of the present invention. System 100 is an OCT system for producing three-dimensional images of a sample at a rate of at least 30 Hz (i.e., in real time). System 100 is analogous to a Michelson interferometer having a sample arm that comprises a scanner for scanning a sample beam along a row of image points on the sample. In some embodiments, system 100 produces three-dimensional images of a sample at less than 30 Hz.

Figure 1B:
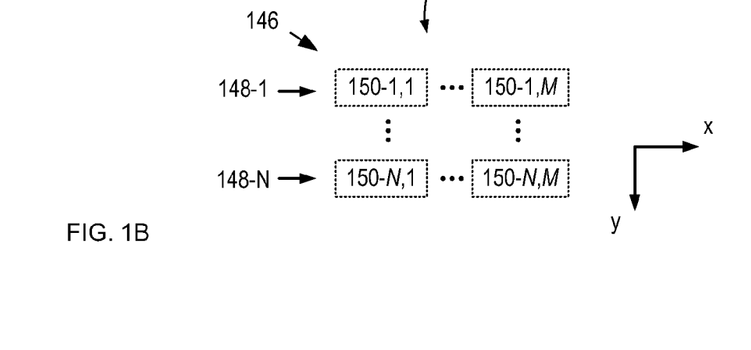
FIG. 1B depicts an array of image points on a surface of a sample in accordance with the illustrative embodiment of the present invention.

FIG. 1B depicts an array of image points on a surface of a sample in accordance with the illustrative embodiment of the present invention. FIG. 1B depicts a portion of surface 146 of sample 130, wherein the portion of surface 146 includes image points 150-1,1 through 150-N,M (referred to, collectively, as image points 150). To simplify the description of the present invention, in the illustrative embodiment, the number of rows of image points, N, is equal to three and the number of image points per row, M, is equal to five. One skilled in the art will recognize that in a typical sample, the number of rows, as well as the number of image points in each row would normally be in the hundreds or thousands.

Figure 2:
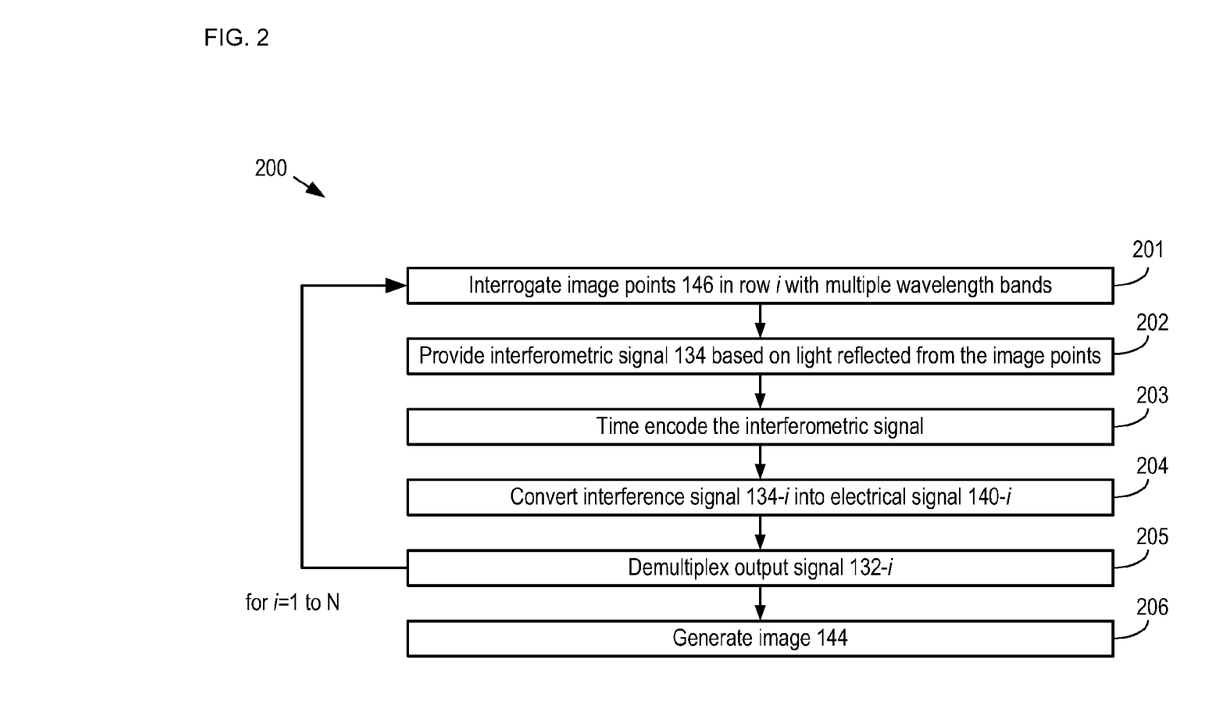
FIG. 2 depicts operations of a method for forming a three-dimensional image of a sample in accordance with the illustrative embodiment of the present invention.

FIG. 2 depicts operations of a method for forming a three-dimensional image of a sample in accordance with the illustrative embodiment of the present invention. Method 200 begins with operation 201, wherein, for each of rows 1 through N, each of image points 150 is interrogated with a comb of wavelength bands.

Figures 3, 4:
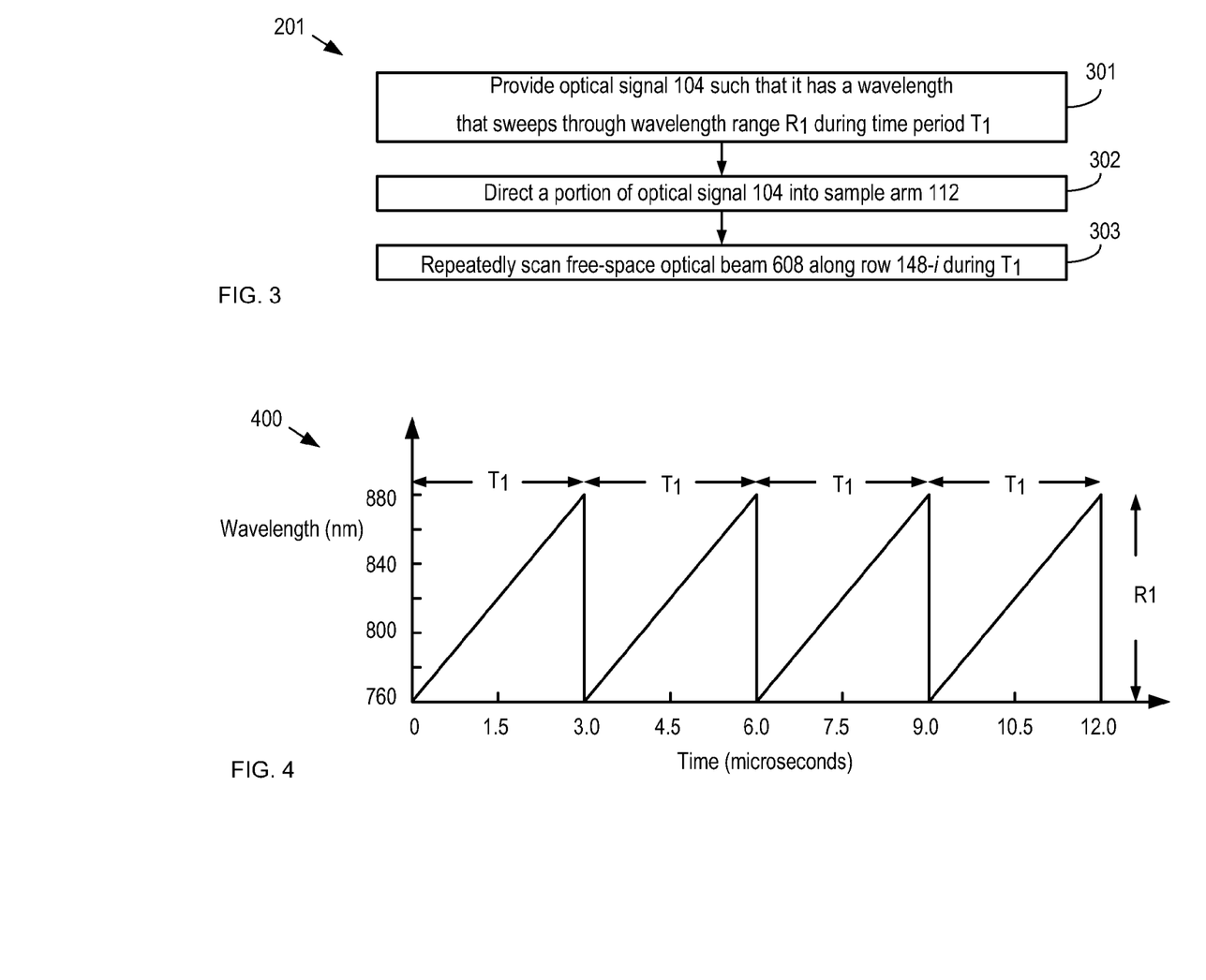
FIG. 3 depicts sub-operations of a sub-method suitable for interrogating a row of image points with a comb of wavelength bands.
FIG. 4 depicts a plot of the wavelength of optical signal 104 versus time.

FIG. 3 depicts sub-operations of a sub-method suitable for interrogating a row of image points with a comb of wavelength bands.

Sub-method 300 begins with sub-operation 301, wherein source 102 provides optical signal 104. FIG. 2 is described with continuing reference to FIGS. 1A and 1B.

Source 102 is a broadband light source optically coupled with an external tunable wavelength filter. Source 102 provides narrow spectral line-width light whose wavelength is continuously swept over wavelength range, $R_1$, which extends from approximately 760 nanometers (nm) to approximately 880 nm. Source 102 provides input optical signal 104 as a periodic signal having a period, $T_1$, which is equal to the time required to sweep the wavelength of source 102 from 760 nm to 880 nm. It will be clear to one skilled in the art, after reading this Specification, how to specify, make, and use source 102. Sources suitable for use with the present invention include narrow line-width, tunable sources such as, without limitation, external cavity tunable lasers, super-luminescent diodes, super-continuum generation light sources, tunable fiber lasers, broad-band sources coupled with tunable wavelength filters, and the like. Further, one skilled in the art will recognize that embodiments of the present invention are suitable for operation in different wavelength regimes.

FIG. 4 depicts a plot of the wavelength of optical signal 104 versus time. Plot 400 depicts input optical signal 104 for a source 102 that operates at a line rate (i.e., sweep frequency) of approximately 333 kHz; therefore, $T_1$ is approximately equal to 3.0 microseconds.

The depth resolution of OCT depends on the temporal coherence characteristics of the light source used. The emergence of a new generation of super-broadband sources, therefore, has facilitated construction of OCT systems with micron-scale resolution. One such super broadband source is the Fourier-domain mode-locking laser (FDML). In some embodiments of the present invention, source 102 comprises an FDML-based laser. FDML-based lasers are well suited for use as source 102 due to their potential for high-speed wavelength tuning over a relatively wide spectral range, while maintaining high power output. For example, FDMLs have been demonstrated that are capable of sweeping their wavelength over a spectral width of nearly 150 nm at frequencies of over 300 kHz. Further, FDMLs have been developed for operation in many different wavelength regimes, including 1000 nm, 1300 nm, and 1500 nm.

At sub-operation 302, a portion of optical signal 104 is directed into sample arm 110.

Source 102 is fiber coupled with splitter/combiner 108 via input fiber 106. Splitter/combiner 108 is a conventional optical splitter/combiner having a split ratio of 50:50. Splitter/combiner 108 receives input optical signal 104 and splits it into optical signal 114 in reference arm 110 and optical signal 124 in sample arm 112. In some embodiments, the split ratio of splitter/combiner 108 is other than 50:50 (e.g., 80:20, 90:10, etc.).

In reference arm 110, splitter/combiner 108 is fiber coupled with lens 118 via reference fiber 116. Lens 118 is a conventional refractive lens that collimates optical signal 114 and launches it into free-space. Optical signal 114 is then reflected by mirror 120 and coupled back into reference fiber 116 by lens 118 as optical signal 122.

In sample arm 112, splitter/combiner 108 is fiber coupled with scanner 128 via sample fiber 126. Scanner 128 collimates optical signal 124 and directs it through free-space to sample 130.

Although the illustrative embodiment comprises an interferometer that is optical fiber based (i.e., the elements of the interferometer are fiber coupled with one another), it will be clear to one skilled in the art, after reading this Specification, how to specify, make, and use alternative embodiments of the present invention wherein at least a portion of system 100 comprises a free-space optical arrangement. In other words, in some embodiments of the present invention, at least one optical element (e.g., source 102, splitter/combiner 108, mirror 120, scanner 128, detector 138, etc.) is optically coupled with system 100 via free space.

At sub-operation 303, scanner 128 repeatedly scans optical signal 124 along each of the M image points in row 148-i.

Figure 5:
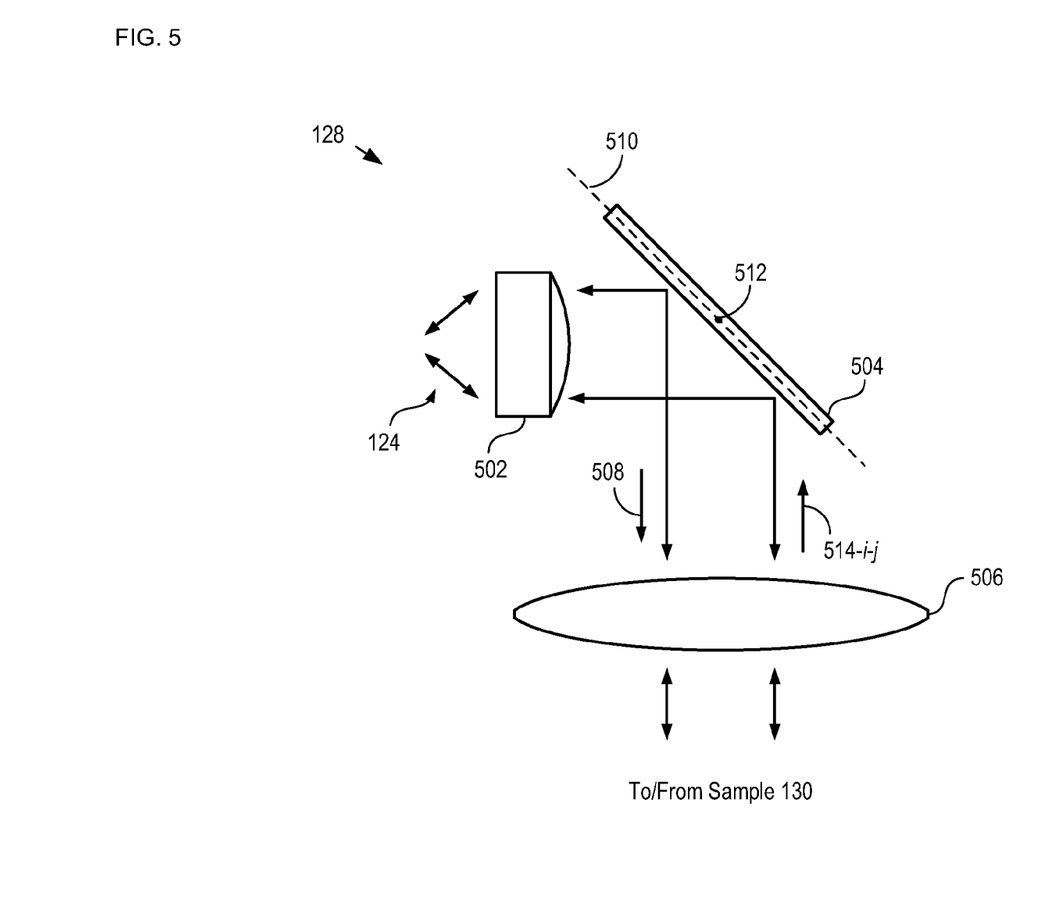
FIG. 5 depicts a schematic drawing of a scanner in accordance with the illustrative embodiment of the present invention.

FIG. 5 depicts a schematic drawing of a scanner in accordance with the illustrative embodiment of the present invention. Scanner 128 comprises lens 502, scanning mirror 505, and lens 506.

Lens 502 is a conventional collimating lens that receives optical signal 124 from sample fiber 126 and collimates it as free-space beam 508.

Scanning mirror 504 is a first surface reflector that is substantially completely reflective for the wavelengths of light included in free-space beam 508. Scanning mirror is rotatable about each of axes 510 and 512, which are substantially orthogonal to each other. As a result, scanning mirror 504 is suitable for receiving free-space beam 508 and directing it at any angle within an included cone of angles.

One skilled in the art will recognize that the size of scanning mirror 504, its scanning speed, and its angular ranges about axes 510 and 512 are matters of design choice and dictated by the intended application of system 100. Scanning mirrors suitable for use with the present invention include, without limitation, two-axis MEMS gimbal-mounted mirrors, pairs of single-axis mirrors, polygon mirrors, galvanometers, and the like.

Lens 506 receives free-space beam 508 from scanning mirror 504 and redirects the beam such that its direction of propagation is substantially normal to the surface of sample 130. Lens 506 enables the optical path of light directed toward sample 130 to share the optical path of light reflected by sample 130 without regard to the angle at which free-space beam 508 hits lens 506. As a result, scanner 128 is able to scan free-space beam 508 along a relatively long path of image points on sample 130 and still couple light reflected from the sample back into sample fiber 126.

Figure 6:
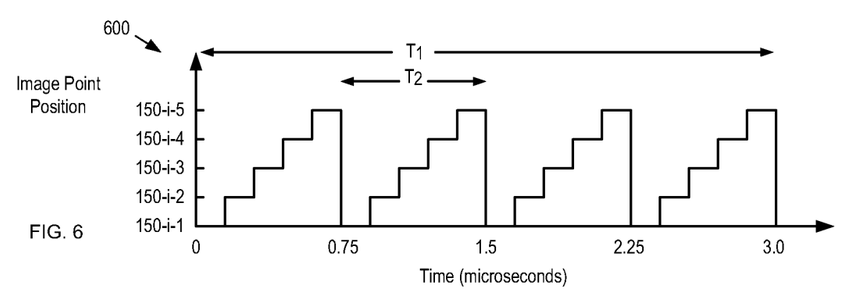
FIG. 6 depicts a plot of scanner position during a sweep period.

FIG. 6 depicts a plot of scanner position during a sweep period. As seen from plot 600, during a single sweep period $T_1$, scanner 128 sequentially directs free-space optical beam 508 to each of image points 150-$i$-1 through 150-$i$-5 in row 148-$i$ during each of four scanning periods, $T_2$. As a result, during a single sweep of the wavelength of optical signal 104 through wavelength range $R_1$, each image point in row 148-$i$ is illuminated four times. Although the illustrative embodiment comprises image points that are arranged in a line and that are scanned in linear fashion, it will be clear to one skilled in the art, after reading this Specification, how to specify, make, and use alternative embodiments of the present invention wherein image points of a sample are scanned in another pattern, such as circular, back-and-forth, triangular, or irregular patterns. Further, one skilled in the art will recognize, after reading this Specification, that in some embodiments, sweep period, $T_1$, can be non-uniform to enable different numbers of image points to be scanned during different sweep periods.

Further, each of the image points in row 148-$i$ is illuminated with light having wavelength bands that substantially span the entire wavelength range, $R_1$. In other words, each of image points 150-$i$-1 through 150-$i$-5 is interrogated by light characterized by a wavelength range that is substantially equal to the wavelength range of input optical signal 104. It should be noted that the wavelength range of the light that illuminates each image point differs from wavelength range, $R_1$, by a small amount (which is based on the value of M and the number of scanning periods, $T_2$, in each sweep period $T_1$); however, this difference is typically negligible. For the purposes of this Specification, including the appended claims, therefore, the wavelength ranges of the wavelength bands that illuminate each image point are defined as substantially equal to $R_1$.

One skilled in the art will recognize that the specific arrangement of scanner 128 represents only one possible approach to optically interrogating a plurality of image points on sample 130. In some embodiments, scanner 130 comprises a diffractive element, such as a diffraction grating or prism, echelle grating, etalon, and the like, which spatially disperses the wavelength bands of optical signal 124 along a row of image points on sample 130. In some embodiments, scanner 128 comprises an electro-optic planar lightwave circuit scanner, such as is described in U.S. Pat. No. 7,720,116, issued May 18, 2010, entitled "Tunable Laser Having Liquid Crystal Waveguide," which is incorporated herein by reference.

Further, one skilled in the art will recognize that scanner 128 does not require motion of an element (e.g., a mirror, etc.) in order to scan free-space optical beam 508 across sample 130. For example, in some embodiments wherein scanner 128 comprises a diffractive element, free-space optical beam 508 scans across the surface of sample 130 as the wavelength of optical signal 124 changes during $T_1$.

Figure 7A:
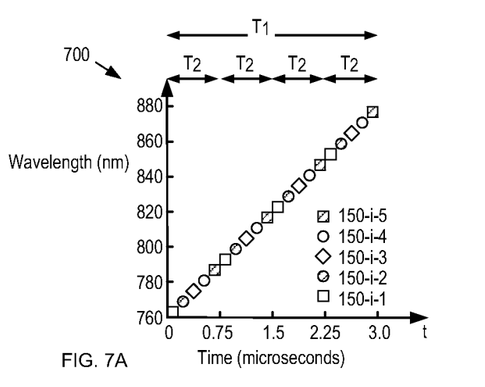
FIG. 7A depicts a plot of an illumination pattern in accordance with the illustrative embodiment of the present invention.

FIG. 7A depicts a plot of an illumination pattern in accordance with the illustrative embodiment of the present invention. Plot 700 shows the relationship between wavelength and image point position as a function of time. Image point position is denoted by symbol, as shown in the legend included in FIG. 7A. As discussed above, during each scanning period, $T_2$, free-space beam 508 is sequentially indexed from image point 150-$i$-1, to image point 150-$i$-2, to image point 150-$i$-3, to image point 150-$i$-4, and to image point 150-$i$-5. In some embodiments, the residence time for the free-space beam at each image point is based on the sampling bandwidth of detector 138. In some embodiments, free-space beam 508 is swept across the image points at a continuous scan rate, rather than in discrete steps between each image point.

Since the wavelength of free-space beam 508 is changing at a constant rate during each scanning period, the wavelength of the wavelength band incident on each image point during each scanning period is different. For example, during the scanning period from t=0 to t=1.5, image point 150-$i$-1 is illuminated by a wavelength band whose center wavelength is approximately 763 nm, image point 150-$i$-2 is illuminated by a wavelength band whose center wavelength is approximately 769 nm, image point 150-$i$-3 is illuminated by a wavelength band whose center wavelength is approximately 775 nm, image point 150-$i$-4 is illuminated by a wavelength band a wavelength band whose center wavelength is approximately 781 nm, and image point 150-$i$-5 is illuminated by light whose center wavelength is approximately 787 nm.

This pattern of illumination continues for each of the remaining scanning periods in sweep period $T_1$. As a result, each image point is illuminated by four different wavelengths over a spectral width that is substantially equal to the spectral width (i.e., wavelength range) of free-space beam 508. For example, over the entire sweep period from t=0 to t=3.0, image point 150-$i$-2 is illuminated by wavelength bands having center wavelengths at approximately 769, 799, 829, and 859 nm. In similar fashion, image point 150-$i$-4 is illuminated by wavelength bands having center wavelengths at approximately 781, 811, 841, and 871 nm. In other words, image points 150-$i$ are illuminated by wavelength bands that are spectrally interleaved.

It should be noted that in some prior-art approaches, such as spectrally encoded confocal microscopy (SECM) and spectral encoding endoscopy (SEE), a swept-source or broadband input optical beam is scanned across a plurality of image points on a sample. In contrast to the present invention, however, such systems continuously scan the input beam across the image points in a row only once during a sweep period. As a result, each image point is illuminated by a continuous wavelength band that has a spectral width that is much smaller than the spectral width of the swept-source signal. In fact, for any one of K image points sampled during a sweep period of a SEE system, for example, the spectral width of the wavelength band that illuminates the image point is equal to 1/K of the spectral width of the swept source.

Figure 7B:
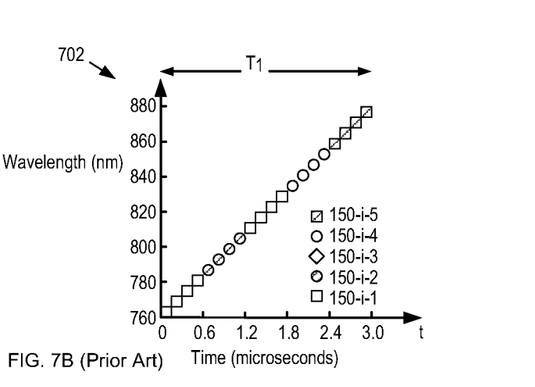
FIG. 7B depicts a plot of an illumination pattern in accordance with the prior-art.

FIG. 7B depicts a plot of an illumination pattern in accordance with the prior-art. Plot 702 shows the relationship between wavelength and image point position as a function of time for a row of image points on sample 130, for the illumination pattern of a SEE system.

Plot 702 clearly demonstrates that the spectral width of the wavelength bands that illuminate any of image points 150-$i$-1 through 150-$i$-5 is smaller than $R_1$ by a factor equal the number of image points in row 148-$i$ (i.e., five, in the example described here). As discussed above and with respect to FIG. 3, the spectral width of free-space optical beam 508, $R_1$, is approximately 120 nm. Image point 150-$i$-1, however, is illuminated by wavelength bands that are clustered together within the wavelength range from approximately 760 nm to approximately 784 nm. The spectral width (i.e., wavelength range) of the light that illuminates image point 150-$i$-1, therefore, is only approximately 24 nm. In similar fashion, image point 150-*i*-5 is illuminated by wavelength bands that are clustered together within the wavelength range from approximately 856 nm to approximately 880 nm. The spectral width (i.e., wavelength range) of the light that illuminates image point 150-*i*-5, therefore, is also only approximately 24 nm. Since depth resolution in an OCT system is based on the spectral width of the light used to illuminate image points, it is clear that the depth resolution of a SEE system is dramatically worse than that of a comparable OCT system in accordance with the present invention.

Returning now to FIG. 3, at sub-operation 304, during sweep period $T_1$, each image point, 150-*i-j* in row 148-*i* reflects light based on its surface and sub-surface structure to produce an optical output signal 514-*i-j*. Optical output signals 514-*i-j* are sequentially coupled back into sample fiber 126 by scanner 128 to collectively define optical output signal 132-*i*.

Returning now to FIG. 2, at operation 202, optical output signal 132-*i* is combined with optical signal 122 at splitter/combiner 108 to produce interferometric signal 134-*i*.

At operation 203, interferometric signal 134-*i* is time encoded. It should be noted that, in the illustrative embodiment, time encoding of interferometric signal 134-*i* occurs inherently by virtue of the manner in which free-space optical beam 508 is scanned across the image points in each row 148. As a result, time encoding of interferometric signal 134-*i* occurs during operations 301 through 304. In some embodiments of the present invention, however, the image points in each row 148-*i* are illuminated with separate combs of wavelength bands in a substantially simultaneous manner, as discussed below and with respect to FIG. 8.

At operation 204, detector 138 converts interference signal 134-*i* into electrical signal 140-*i*.

Detector 138 is a photodetector having sampling bandwidth sufficient to sample output signal 132-*i* at a rate that satisfies the Nyquist sampling criterion. In the example shown here, therefore, detector 138 has a sampling bandwidth equal to or greater than $2*M/T_1$, or approximately 3.3 MHz. Some embodiments of the present invention include a detector having a sampling bandwidth that exceeds 1 GHz.

At operation 205, processor 142 demultiplexes output signal 132-*i* to separate the information corresponding to each image point 150-*i-j* and resamples the information to convert it from a signal based on time into a signal based on wavenumber. Processor 142 then applies a Fourier transform algorithm to generate a Fourier spectrum corresponding to each image point, from which the depths of sub-surface features at image point 150-*i-j* are computed.

Although in the illustrative embodiment, system 100 interrogates sample 130 via uniformly spaced wavelengths, in some embodiments of the present invention, system 100 interrogates sample 130 via optical signals that are uniformly spaced in wavenumber. In such embodiments, therefore, it is not necessary to resample the information corresponding to each image point prior to applying a Fourier transform algorithm to it.

Operations 201 through 205 are repeated for each row 148-*i*, for i=1 to N.

At operation 206, processor 142 aggregates the depth information of each image point 150-*i-j* into image 144, a three-dimensional image of the sub-surface structure of sample 130.

Figure 8:
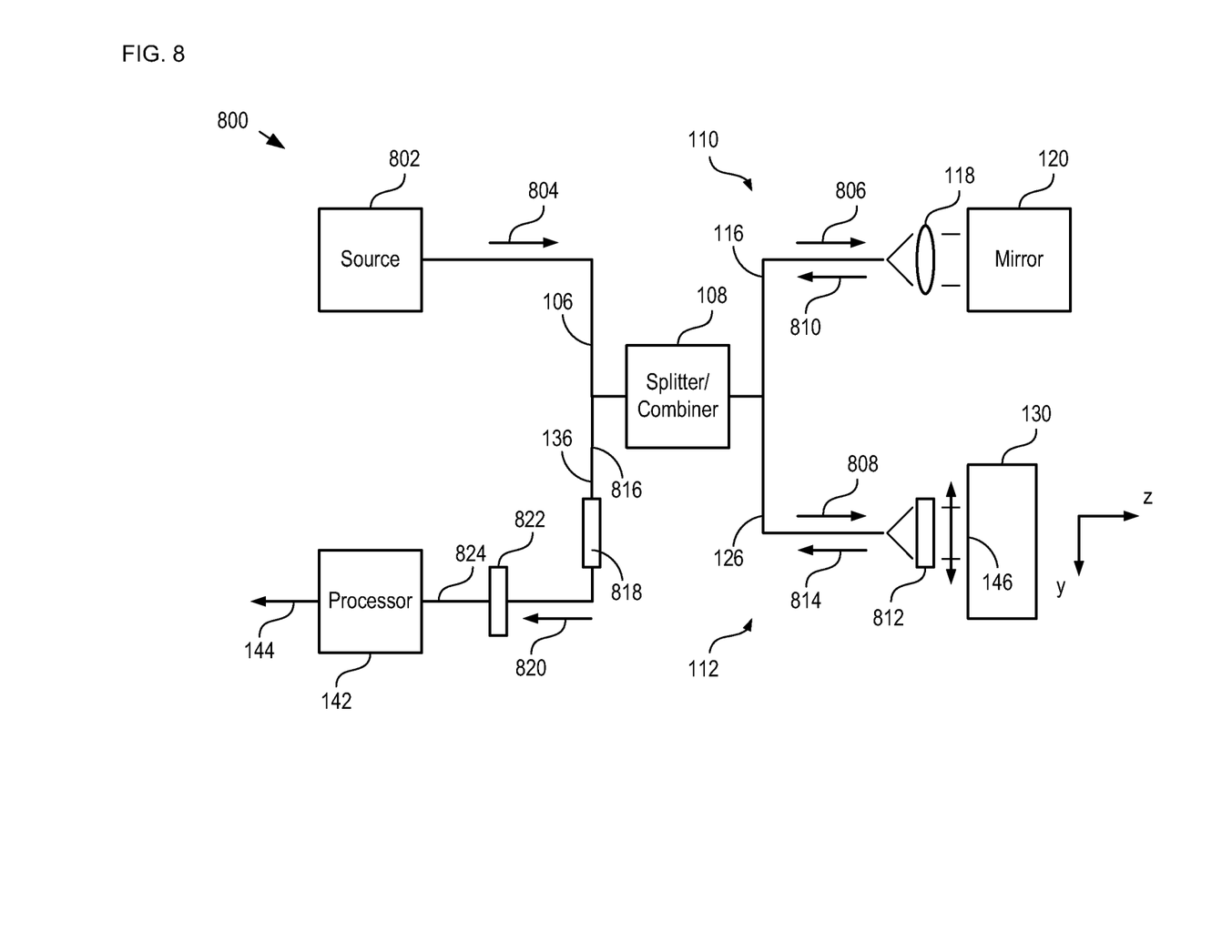
FIG. 8 depicts a schematic diagram of a portion of an OCT system in accordance with an alternative embodiment of the present invention.

FIG. 8 depicts a schematic diagram of a portion of an OCT system in accordance with an alternative embodiment of the present invention. System 800 is an OCT system that optically interrogates each image point in a row of image points on a sample in a substantially simultaneous manner. Like system 100, system 800 is analogous to a Michelson interferometer having a sample arm that comprises a scanner for scanning a sample beam along a row of image points on the sample. System 800, however, time encodes the resultant interferometric signal from each row of image points after the generation of the interferometric signal. System 800 comprises source 802, splitter/combiner 108, spatial disperser 812, chromatic disperser 818, detector 822, and processor 142.

In system 800, broadband light signal 804 is provided to spatial disperser 812 by source 802.

Source 802 is a broadband light source that provides light signal 804, which includes a continuous band of wavelengths over wavelength range R1. Light signal 804 is split into reference signal 806 and sample signal 808 at splitter/combiner 108.

In reference arm 110, splitter/combiner 108 is fiber coupled with lens 118 via reference fiber 116. Lens 118 collimates optical signal 806 and launches it into free-space. Optical signal 806 is then reflected by mirror 120 and coupled back into reference fiber 116 by lens 118 as optical signal 810.

In sample arm 112, sample signal 808 is received as a free-space optical signal at spatial disperser 812.

Spatial disperser 812 distributes the wavelength bands of light signal 804 over the M image points 150 in row 148-*i* such that each image point 150 receives a plurality of wavelength bands, wherein the wavelength bands received by each image point span a wavelength range substantially equal to R1, and wherein the wavelength bands received by all of the image points are collectively spectrally interleaved.

In some embodiments, spatial disperser 812 is a virtually imaged phase array (VIPA). In some embodiments, spatial disperser 812 comprises one or more different dispersive elements that are collectively suitable for receiving a broadband light signal and dispersing it as a plurality of spatially distributed spots of light, wherein each comprising a comb of wavelength bands, and wherein the wavelength bands over all the spots of light are collectively spectrally interleaved such that each spot of light includes light that spans substantially the same wavelength range as that of light signal 814 (i.e., R1).

Each image point, 150-*i-j* in row 148-*i* reflects light based on its surface and sub-surface structure to produce optical output signal 814-*i-j*. Optical output signals 814-*i-j* are substantially simultaneously coupled back into sample fiber 126 by spatial disperser 812 to collectively define optical output signal 814-*i*.

At splitter/combiner 108, optical output signal 814-*i* is combined with optical signal 810 at to produce interferometric signal 816-*i*.

Since all of optical output signals 814-*i-j* are generated simultaneously, the wavelength bands in the interferometric signal are temporally coincident. As a result, interferometric signal 816-*i* is not time-encoded (i.e., it lacks frequency-time mapping).

In order to time encode the interferometric signal 816-*i* (during operation 203, described above and with respect to FIG. 2), it is passed through chromatic disperser 818. Chromatic disperser 818 is a length of chromatically dispersive optical fiber that induces a wavelength-dependent propagation delay on the spectral information in interferometric signal 816-*i*. In some embodiments, chromatic disperser 818 is a chromatically dispersive element other than a length of chromatically dispersive optical fiber.

Once interferometric signal 816-*i* is time-encoded, it is sampled by detector 822 to produce electrical signal 824. Detector is analogous to detector 140 discussed above. Processor 142 then processes electrical signal 824 and generates a three-dimensional image of sample 130 as described above and with respect to FIG. 1. In some embodiments, such as when system 800 is arranged to image sample 130 at high speed, system 800 includes optical amplification to improve the sensitivity of the system.

It should be noted that system 800 has some similar characteristics as prior art imaging approaches, such as Serial Time-Encoded Amplified Microscopy (STEAM). STEAM systems have been developed for high-speed imaging of a two-dimensional area using a single-pixel detector. In a STEAM system, pulsed light from a broadband source is spectrally dispersed in two dimensions using a spatial disperser and made incident on the sample, wherein each wavelength in the source illuminates a different image point (i.e., spatial position is spectrally encoded). Reflected light from the plurality of image points are collected by a fiber and enters a chromatically dispersive element where, by chromatic dispersion, the pulse is broadened in time. In most instances, the dispersion element is a fiber that is pumped by a second laser so that the reflected light undergoes amplification to increase the strength of the signal. The output of the dispersion element is a pulse of long duration that is sent to a single-pixel detector with a high bandwidth. The pulse is sampled in time using a high-speed digitizer.

In contrast to system 800, however, STEAM systems are not suitable for OCT applications and differ from system 800 in several important ways. First, in a STEAM system, each image point is interrogated by a single wavelength (or wavelength band). In embodiments of the present invention, each image point is interrogated by a plurality of wavelength bands. Second, STEAM systems are inherently incapable of spectrally interleaving the wavelength bands incident on a plurality of image points. In a STEAM system, such spectral interleaving is neither possible nor necessary because each image point is interrogated with a single wavelength band. In embodiments of the present invention, however, spectral interleaving is essential and enables interrogation of each image point over a large wavelength range, which preserves high axial resolution. Third, STEAM systems do not use an interferometer arrangement, which is an essential characteristic of all OCT systems. Therefore, prior-art STEAM systems cannot generate OCT data and do not use the same image processing algorithms that are used in OCT. As a result, STEAM systems have no depth-selectivity and cannot discriminate sub-surface features at an image point.

It is to be understood that the disclosure teaches just one example of the illustrative embodiment and that many variations of the invention can easily be devised by those skilled in the art after reading this disclosure and that the scope of the present invention is to be determined by the following claims.

What is claimed is:

1. A method for forming an image of a sample via optical coherence tomography, the method comprising:
   interrogating a first image point of M image points on the sample with a first plurality of wavelength bands that substantially collectively span a first wavelength range, wherein the first image point reflects a first reflected signal that is based on surface and sub-surface structure at the first image point;
   interrogating a second image point of the M image points on the sample with a second plurality of wavelength bands that substantially collectively span the first wavelength range, wherein the second image point reflects a second reflected signal based on surface and sub-surface structure at the second image point, and wherein the second plurality of wavelength bands and the first plurality of wavelength bands are spectrally interleaved;
   forming an interferometric signal based on M reflected signals, wherein the M reflected signals include the first reflected signal and the second reflected signal;
   time encoding the interferometric signal; and
   providing M output signals, wherein each of the M output signals is based on a different one of the M image points, and wherein each of the M output signals is provided by sampling the interferometric signal at a first detector.

2. The method of claim 1 further comprising forming an image of the sample, wherein the image is based on the plurality of output signals.

3. The method of claim 1 wherein the interferometric signal is time encoded by operations comprising:
   providing an input optical signal that is periodic with a first period, $T_1$, wherein the input optical signal comprises input light having an wavelength that sweeps from a first wavelength to a second wavelength over a first wavelength range during each first period; and
   scanning the input optical signal over the plurality of image points during each of a plurality of second periods, $T_2$, wherein the first period includes the plurality of second periods.

4. The method of claim 3 further comprising the first detector such that the first detector has a sampling bandwidth that is greater than or equal to $2*M/T_1$.

5. The method of claim 1 wherein the interferometric signal is time encoded by conveying the interferometric signal through a chromatically dispersive optical fiber.

6. The method of claim 1 further comprising:
   interrogating a third image point of the M image points on the sample with a third plurality of wavelength bands that substantially collectively span the first wavelength range, wherein the third image point reflects a third reflected signal that is based on surface and sub-surface structure at the third image point;
   wherein the M reflected signals further include the third reflected signal; and
   wherein the first plurality of wavelength bands, the second plurality of wavelength bands, and third plurality of wavelength bands are spectrally interleaved.

7. A method for forming an image of a sample via optical coherence tomography, the method comprising interrogating each of a plurality of rows that each include a plurality of image points on the sample, wherein each row is interrogated by operations comprising:
   providing an input optical signal that is periodic with a first period, $T_1$, wherein the input optical signal comprises input light having an wavelength that sweeps from a first wavelength to a second wavelength over a first wavelength range during each first period;
   scanning the input optical signal over the plurality of image points during each of a plurality of second periods, $T_2$, wherein the first period includes the plurality of second periods; and
   providing a plurality of output optical signals, wherein each output optical signal uniquely comprises input light reflected by a different image point, and wherein each output optical signal is based on input light reflected during each of the plurality of second periods.

8. The method of claim 7 further comprising generating a plurality of output signals, wherein each of the plurality of output signals is based on a different one of the plurality of output optical signals.

9. The method of claim 7 wherein the second period is a sub-multiple of the first period.

10. The method of claim 7 wherein each of the plurality of image points receives light over a range of wavelengths that is substantially equal to the first wavelength range.

11. The method of claim 7 wherein the input optical signal is scanned over the plurality of image points via a scanner comprising a mirror.

12. The method of claim 7 wherein the input optical signal is scanned over the plurality of image points via a scanner comprising a diffractive element.

13. The method of claim 7 wherein the plurality of rows are interrogated by linear raster scanning.

14. The method of claim 7 wherein the plurality of rows are interrogated by radial raster scanning.

15. The method of claim 7 further comprising receiving each of the plurality of output optical signals at a first detector having a bandwidth that is greater than or equal to $2*M/T_1$, wherein M is equal to the number of image points in the plurality of image points.

16. The method of claim 7 further comprising receiving each of the plurality of output optical signals at a first detector having a bandwidth that is greater than or equal to $2*N*M*30$ Hz, wherein N is equal to the number of rows in the plurality of rows, and wherein M is equal to the number of image points in the plurality of image points.

17. A swept-source optical coherence tomography system for providing an image of a sample, the system comprising:
a light source, wherein the light source provides light having a wavelength that sweeps across a first wavelength range during a first period, $T_1$;
an interferometer comprising a sample arm;
a scanner, wherein the scanner repeatedly scans a first optical signal comprising light from the light source across a first row comprising a plurality of image points on the sample during the first period, and wherein the image points collectively receive light having wavelengths over the wavelength range in an interleaved fashion; and
a first detector that receives a plurality of output optical signals, wherein each of the output optical signals comprises light uniquely reflected from a different one of the image points, and wherein the first detector generates a plurality of output signals that are based on the plurality of output optical signals.

18. The system of claim 17 wherein each of the optical output signals includes a range of wavelengths that is substantially equal to the first wavelength range.

19. The system of claim 17 wherein the first detector has a bandwidth that is greater than or equal to $2*M/T_1$, wherein M is the number of image points in the plurality of image points.

20. The system of claim 17 further comprising scanning the first optical signal across a plurality of rows that comprises the first row, wherein the first detector has a bandwidth that is greater than or equal to $2*N*M*30$ Hz, where N is equal to the number of rows in the plurality of rows, and M is equal to the number of image points in each of the plurality of rows.

* * * * *